United States Patent
Brackett

(10) Patent No.: US 6,618,060 B1
(45) Date of Patent: Sep. 9, 2003

(54) METHOD AND APPARATUS FOR FORMATTING DIGITAL IMAGES IN ACCORDANCE WITH USER-SELECTED COMMUNICATIONS STANDARD

(75) Inventor: Charles Cameron Brackett, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/557,594

(22) Filed: Apr. 24, 2000

(51) Int. Cl.$^7$ ................................................ G09G 5/00
(52) U.S. Cl. ........................ 345/810; 345/840; 345/735
(58) Field of Search ................................ 345/716, 717, 345/718, 719, 720, 721, 722, 760, 771, 735, 810, 848; 709/201; 358/1.15

(56) References Cited

U.S. PATENT DOCUMENTS

| | | | | |
|---|---|---|---|---|
| 5,668,998 A | * | 9/1997 | Mason et al. ................ | 717/104 |
| 5,671,353 A | * | 9/1997 | Tian et al. .................... | 714/48 |
| 6,117,079 A | * | 9/2000 | Brackett et al. ............. | 600/437 |
| 6,210,327 B1 | * | 4/2001 | Brackett et al. ............. | 600/437 |
| 6,348,793 B1 | * | 2/2002 | Balloni et al. ............... | 324/309 |
| 6,351,547 B1 | * | 2/2002 | Johnson et al. ............. | 382/128 |
| 6,388,687 B1 | * | 5/2002 | Brackett et al. ............. | 345/810 |
| 6,417,870 B1 | * | 7/2002 | Brackett et al. ............. | 345/771 |

* cited by examiner

*Primary Examiner*—John Cabeca
*Assistant Examiner*—Shawn M. Becker
(74) *Attorney, Agent, or Firm*—Ostrager Chong & Flaherty LLP

(57) ABSTRACT

Method and apparatus for configuring computer tasks which construct data objects. The system user is able to configure these tasks by the simple expedient of clicking on a toggle switch displayed on a user interface screen or menu. In response to operation of the toggle switch, a selected one of a pair of attribute control files associated with the particular task will be utilized during object construction. The menu contains a list of the activated configured remote devices for the particular imaging system. Next to each device name is a virtual toggle switch (defaulted to OFF). In the OFF state, the task will be configured in accordance with the first attribute control file which is compliant with a first communications standard. If the user toggles the switch for a particular device to ON (this can be done on a per device basis), then the task will be configured in accordance with the second attribute control file which is compliant with a second communications standard. By toggling switches on the menu, the user is able to tell the system which attribute control file to use (to configure a task) for which remote device.

16 Claims, 6 Drawing Sheets

```
                    ACTIVE DEVICE CONFIGURATION
_____

NAME            IHE TAGS
  1.    CTW             [OFF] ── 56
  2.    RADWORKS        [OFF]
  3.    EFILM           [OFF]
  4.                    [OFF]
  5.                    [OFF]
  6.                    [OFF]
  7.                    [OFF]
  8.                    [OFF]
  9.                    [OFF]
 10.                    [OFF]

ROI    Size to page
  TKBL/RET to position    SET to select          EXIT to save
```

DEVICE CONFIGURATION         PAGE    1 of 11

NAME     [PRINTER A]                        AE TITLE [        ]
IP ADDR  [0].[0].[0].[0]
PORT     [104]                 COLOR [COLOR]         DEVICE TYPE [PRINTER]
RETRIES  [1]                   RETRY INTERVAL [10] SEC   TIMEOUT [10] SEC — 48
ECHO     [ECHO ON]             ACTIVATE [YES] — 50

PRINTER SETUP
FORMAT           [3 x 5] — 52              ORIENTATION   [PORTRAIT]
SIZE             [8in x 10in]              MEDIA TYPE    [PAPER]
COPIES           [1]                       BORDER        [BLACK]
PRIORITY         [HIGH]                    EMPTY         [BLACK]
MIN DENSITY      [0]                       MAX DENSITY   [0]
TRIM             [NO]                      DESTINATION   [MAGAZINE]
MAGNIFICATION    [REPLICATE]
SMOOTH           [NONE]
FILM SESSION LABEL

CONFIGURATION STRING    [                    ]
                        [                    ]

WORKLIST SETUP                             STORAGE SETUP
POLLING RATE    [0] MINUTES                TYPE   [AUTOMATIC]
                                           LIVE IMAGING [OFF]

TKBL/RET TO POSITION    SET TO SELECT    ROI  SIZE TO PAGE
                                              EXIT TO SAVE

DEVICE ACTIVATION

| | NAME | ACTIVE |
|---|---|---|
| 1 | PRINTER A | YES — 54 |
| 2 | PRINTER B | YES |
| 3 | STORAGE A | YES |
| 4 | STORAGE B | NO |
| 5 | PRINTER X | NO |
| 6 | PRINTER Y | NO |
| 7 | | NO |
| 8 | | NO |
| 9 | | NO |
| 10 | | NO |
| 11 | | NO |
| 12 | | NO |
| 13 | | NO |
| 14 | | NO |
| 15 | | NO |
| 16 | | NO |
| 17 | | NO |
| 18 | | NO |
| 19 | | NO |
| 20 | | NO |

TKBL/RET TO POSITION    SET TO SELECT    ROI SIZE TO PAGE
                                          EXIT TO SAVE

ACTIVE DEVICE CONFIGURATION

| | NAME | IHE TAGS |
|---|---|---|
| 1. | CTW | OFF ―56 |
| 2. | RADWORKS | OFF |
| 3. | EFILM | OFF |
| 4. | | OFF |
| 5. | | OFF |
| 6. | | OFF |
| 7. | | OFF |
| 8. | | OFF |
| 9. | | OFF |
| 10. | | OFF |

TKBL/RET to position   SET to select   ROI Size to page
                                       EXIT to save

FIG.6

METHOD AND APPARATUS FOR FORMATTING DIGITAL IMAGES IN ACCORDANCE WITH USER-SELECTED COMMUNICATIONS STANDARD

FIELD OF THE INVENTION

This invention generally relates to imaging systems used in medical diagnostics. In particular, the invention relates to the transfer of digital images from an ultrasound imaging system over a network to remote devices for archiving, viewing and/or printing.

BACKGROUND OF THE INVENTION

Conventional ultrasound imagers create two-dimensional images of biological tissue by scanning a focused ultrasound beam in a scan plane and for each transmitted beam, detecting the ultrasound wave energy returned along a respective scan line in the scan plane. A single scan line (or small localized group of scan lines) is acquired by transmitting focused ultrasound energy at a point, and then receiving the reflected energy over time. A B-mode ultrasound image is composed of multiple image scan lines. The brightness of a pixel on the display screen is based on the intensity of the echo returned from the biological tissue being scanned. The outputs of receive beamformer channels are coherently summed to form a respective pixel intensity value for each sample volume in the scanned object. These pixel intensity values are log-compressed, scan-converted and then displayed as a B-mode image of the anatomy which was scanned.

If the ultrasound probe is swept over an area of body, a succession of image frames (corresponding to spaced slices intersecting the body being examined) can be displayed on the monitor. In one type of ultrasound imaging system, a long sequence of the most recent images are stored and continuously updated automatically in a cine memory on a first-in, first-out basis. The cine memory is like a circular image buffer that runs in the background, capturing image data that is displayed in real time to the user. The cine memory acts as a buffer for transfer of images to digital archival devices via the host computer. When the user freezes the system (by operation of an appropriate device on an operator interface), the user has the capability to view image data previously captured in cine memory. The image loop stored in cine memory can be reviewed on the display monitor via trackball control incorporated in the operator interface, and a section of the image loop can be selected for hard disk storage. Any acquired or projected image can be stored internally on the system hard disk or on a magneto-optical disk (MOD) inserted in a disk drive.

In addition to storing images internally, modern imaging systems need to be able to transfer images to various types of remote devices via a communications network. To successfully transfer images, the relevant networking features of the imager must be compatible with the networking features of the destination remote device. In particular, the imager must place the data to be transferred in a format which can be handled by the destination remote device. An attempt to accomplish the foregoing is the adoption of the DICOM (Digital. Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

The DICOM system is based on the client/server concept. The device which uses a service (on objects) is the client device, while the device which provides the service is the server device. The client device is referred to as a Service Class User (SCU), while the server device is referred to as a Service Class Provider (SCP). The SCU sends a Service Request to the SCP over a local area network (LAN). The SCP sends back a response to the SCU over the same LAN. If the response is affirmative and a communications syntax is agreed upon, an association between the SCU and the SCP is opened and data can be transferred between the two devices. In the DICOM system a device is not limited to one role: it can be both SCU and SCP at different times.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a LAN to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In order to accomplish image transfer, the ultrasound imaging system must know the configuration of the destination remote device prior to attempting to communicate with that device. The configuration data for the destination remote device is typically inputted to the ultrasound imager during software installation by a field engineer, although the DICOM network can be configured at any time. When the imager receives an instruction to transmit data to a particular remote device from the system operator, the imager software converts the image data to be transferred into the DICOM format required by the destination remote device, based on the configuration data for that device stored in system memory. The imager also sends a request over the network to the destination remote device to open an association, i.e., to connect the imager to the destination remote device. If the remote device responds in the affirmative, the imager and remote device then agree on which device will act as the server and which as the client. The ultrasound imager also selects the appropriate encoding syntax from those accepted by the remote device. Other communication parameters are also negotiated.

After the DICOM communications protocol has been settled, the association is opened and the imager attempts to send the DICOM-formatted image file (object) to the remote device via the network. The transfer is done in the background while scanning or other operator activities continue. If the remote device is a storage device, each image file is transferred singly in response to a Send request inputted by the operator. If the remote device is a printer configured to print multi-image film, then a number of images are accumulated to make up a multi-image film and an association is opened in response to a Send instruction when a number of images sufficient to fill the multi-image film have been accumulated.

The remote device to which the ultrasound imager sends data can be a printer, a storage device or other device. If the operator interface of the imager has only one configurable Print/Store button, then that button will be configured to initiate data transfer to the destination remote device. The configuration data for the remote device will indicate the type of device to the imager and then the imager will format the data being transferred accordingly. If the operator interface has multiple Print/Store buttons, then each button can be configured to initiate data transfer to a respective remote device. Data transfer to any one of those configured remote devices can then be initiated by pressing the appropriate Print/Store button.

In addition to the digitized image (i.e., pixel data), the DICOM object transferred from the ultrasound imager also includes attribute information. For example, the attribute information may include patient attributes (e.g., patient name and patient identification number), exam attributes (e.g., exam description and exam date), series attributes (e.g., modality type and series date), and image attributes (e.g., image type and numbers of rows and columns). Each attribute has a name, a value representation and a tag. A tag is a number unique to the attribute, e.g., (0040,0100), and is used to identify the attribute. (Different systems use different tags for the same attribute name, which gives rise to incompatibility, as described in more detail hereinafter.) The value representation defines what type of value the attribute can have (e.g., a 64-character string, binary data, etc.).

In accordance with DICOM standards, there are three types of attributes. Type 1 comprises attributes which are mandatory and must always be present with a value; Type 2 comprises attributes which are mandatory but are allowed to be empty; and Type 3 comprises attributes which are optional and are also allowed to be empty. An incompatibility between two devices may arise, for example, if the receiving device requires that a Type 3 attribute be transmitted while the sending device does not include that attribute in its transmission. As a result, even if both devices are configured in accordance with current DICOM standards, the data transfer cannot occur. Thus, even mutual conformance to DICOM standards does not guarantee that two devices can be compatibly connected to each other.

This problem is complicated by the existence of more than one DICOM standard, namely, the DICOM 98 (old) and DICOM 99 (new) standards, having different attribute requirements. Not all existing remote devices can handle the new attribute requirements. The result is that a conventional imaging system is unable to communicate with all remote devices. In particular, the imaging system is able to communicate with remote devices configured to accept the new DICOM attributes, but is unable to communicate with remote devices configured to accept only the old DICOM attributes.

U.S. patent application Ser. No. 09/300,966, filed on Apr. 28, 1999, discloses an imaging system comprising means for turning off or turning on any DICOM attribute to facilitate communication with a particular remote device. This is accomplished by providing an Attribute Control File which is programmable. However, this feature can be utilized only by the few persons who know which DICOM attributes to turn off. The problem is further complicated because some of these attributes are dependent on other attributes and are order sensitive. Therefore, turning one attribute off without turning off an attribute dependent on the first attribute or changing the order of a sequence of attributes can cause even more problems. This complex arrangement of attributes and their dependencies are described in a 14-volume reference set known as the DICOM 3.0 standard. Service people do not have a copy of this reference set and will not get a copy of this set, because it is very expensive and too complex for the service engineer.

Thus there is a need for a method by which an imaging system user can simply configure the attributes which an imaging system will send to a particular remote device without knowing or inquiring which attributes that particular remote device requires.

SUMMARY OF THE INVENTION

The present invention is incorporated in an imager which is programmed with at least one DICOM task for constructing objects to be transferred to a remote device. The imager may comprise multiple DICOM tasks for communicating with a respective multiplicity of remote devices. Each DICOM task is configurable by the user to construct objects compatible with a particular remote device, e.g., a storage device or printer. Each configured remote device can then be "activated", with the understanding that the term "activation", as used in this context, means that the imager has a DICOM task configured for that remote device, not that the remote device itself is in any sense remotely activated by the imager.

In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements (i.e., tags) of the particular remote device destined to receive that DICOM object.

Each Attribute Control File, in ASCII format, is a mapping of which attributes should be included and which attribute tags should be used in every image sent to the remote device associated with that Attribute Control File. Each DICOM task will convert each image file into a DICOM object having the acquired image data from the image file as well as the attribute data dictated by the Attribute Control File associated with that DICOM task. The data for a particular attribute may be taken from either the image file or from the Attribute Control File during construction of the DICOM object by the DICOM task.

In accordance with a further feature of the preferred embodiment, the host computer is programmed with an Attribute Control Engine which controls the inclusion of particular attributes and attribute tags in the DICOM objects constructed by each DICOM task. In particular, in response to queries from a DICOM task, the Attribute Control Engine will instruct that DICOM task concerning which attributes and what attribute tags should be included in the DICOM object being constructed. The Attribute Control Engine in turn obtains that information from the Attribute Control File associated with that DICOM task.

In accordance with the preferred embodiment of the present invention, each DICOM task constructs DICOM objects by incorporating attribute data for tags identified in a selected one of a pair of Attribute Control Files. Each DICOM task has a pair of Attribute Control Files associated therewith. The user can select either one of these two Attribute Control Files, depending on the requirements of the particular remote device to which the image is being transferred, by the simple expedient of operating a switch.

In the preferred embodiment, this is accomplished via a user interface screen or menu which appears on the display monitor of the imaging system. This menu contains a list of the activated configured remote devices for the particular imaging system. Next to each device name is a virtual toggle switch (defaulted to OFF). In the OFF state, the DICOM task will be configured in accordance with the first Attribute Control File which is compliant with a first communications standard, e.g., the DICOM 98 standard. If the user toggles the switch for a particular device to ON (this can be done on a per device basis), then the DICOM task will be configured in accordance with the second Attribute Control File which is compliant with a second communications standard, e.g., the DICOM 99 standard, and in particular, the IHE (Integrating Healthcare Enterprises) technical framework employing the DICOM 99 standard. These files are installed on the imaging machine. By toggling switches on an Active Device Configuration menu, the user is able to tell the system which Attribute Control File to use (to configure a DICOM task) for which remote device.

In accordance with the preferred embodiment, each DICOM task has two Attribute Control Files associated therewith, each Attribute Control File identifying the attributes and attribute tags required for compatibility with respective communications standards. As in the case of the DICOM 98 and DICOM 99 standards, one communications standard has different attribute requirements than the other. The first Attribute Control File is designed to conform to the first communications standard, while the second Attribute Control File is designed to conform to the second communications standard. In addition, the first Attribute Control File is programmable to allow the corresponding DICOM task to be configured to be compliant with a particular remote device within the framework of the first communications standard, i.e., the DICOM 98 standard.

As presently embodied, the second communications standard is the IHE technical framework, which utilizes two existing standards: DICOM 99 on the modality side and HL-7 on the information side. The purpose of the IHE project is to organize the utilization of existing standards to create better synergy among information, imaging, and peripheral medical computer systems. Without this initiative, imaging vendors could be compliant in the DICOM standard, but still pass different information. Further, expected behavior not defined by the standards are properly described by the IHE standards. This will help an institution when trying to create a complete computerized networked solution made up of varying vendors. If all vendors subscribe to the IHE technical framework, then the institution can be guaranteed that all systems will work together properly and as expected. Since the second Attribute Control File is intended to contain all of the attribute tags required by the IHE technical framework and since the first Attribute Control File is programmable to allow customization by the field service engineer, the second Attribute Control File does not need to be, but certainly could be, programmable to allow customization by the field service engineer. At a minimum, the second Attribute Control File should be upgradeable to reflect changes in the IHE technical framework.

The invention disclosed herein greatly simplifies the DICOM compatibility problems associated with the new DICOM 99 attribute tags (potentially problematic tags for remote devices that cannot handle them) by associating them with a term (i.e., "IHE") more familiar to the institution and allowing the user to simply turn those tags off or on without really having to know what tags are new and what tags are old. It is a simple one-switch effort on a per device basis.

Although the disclosure of the preferred embodiment makes reference to the DICOM 98 and DICOM 99 communications standards, it will be readily appreciated by persons skilled in the art that the invention has application in any imaging system which must comply with two distinct communications standards. The invention disclosed herein relates generally to imaging systems which acquire images that need to be sent to remotely located devices via a network. Although the disclosed preferred embodiment is an ultrasound imaging system, the invention has application in other types of imaging systems. Furthermore, although the preferred embodiment of the invention communicates with remote devices using the DICOM standard, the invention has application with any digital image communications standard or protocol.

BRIEF DESCRIPTION OF THE DRAWINGS

FIG. 4 is a schematic reproducing a "Device Configuration" menu which can be called up on the display monitor during configuration of the imaging system in accordance with the preferred embodiment.

FIG. 5 is a schematic reproducing a "Device Activation" menu which can be used to activate selected configured remote devices in accordance with the preferred embodiment.

FIG. 6 is a schematic reproducing a "Active Device Configuration" menu which can be used to select either of a respective pair of configurations for each DICOM task corresponding to corresponding activated remote devices in accordance with the preferred embodiment of the invention.

DETAILED DESCRIPTION OF THE PREFERRED EMBODIMENTS

Figure 1:
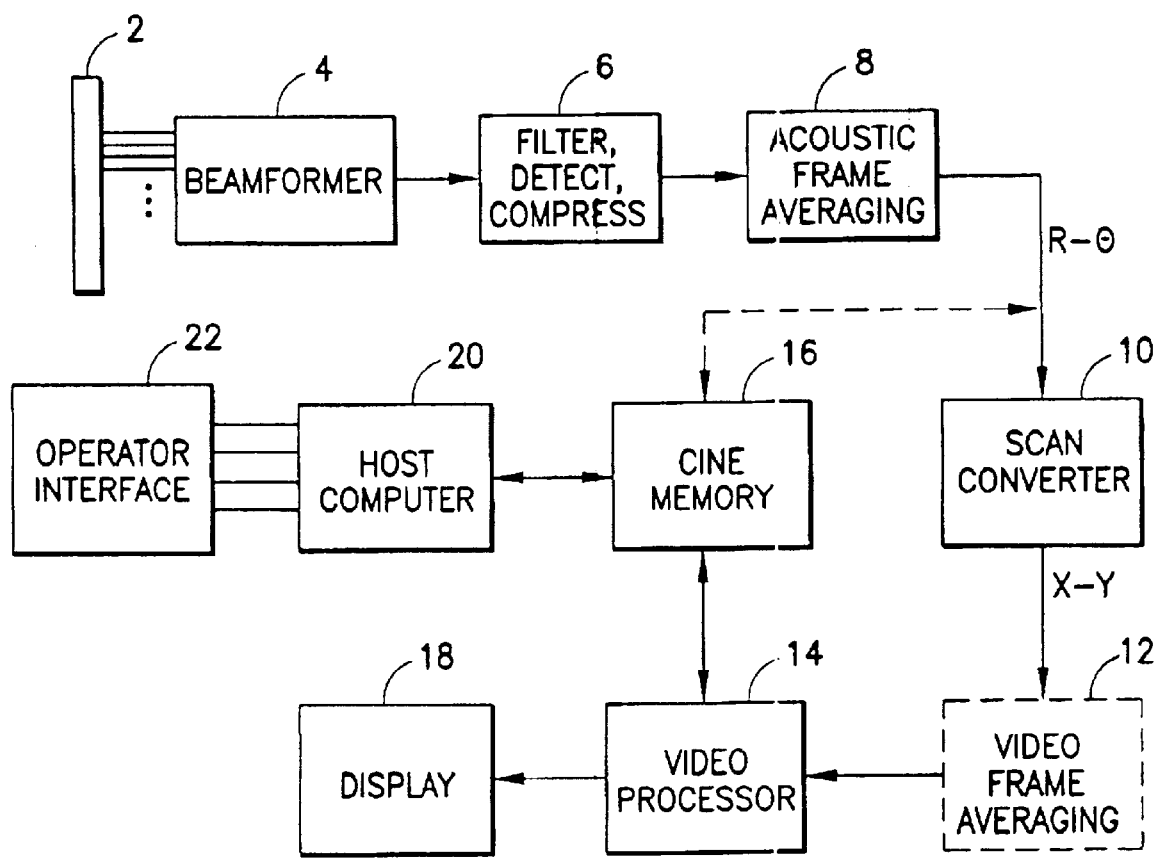
FIG. 1 is a block diagram showing a conventional ultrasound imaging system of the type which can be programmed to have DICOM capability.

FIG. 1 shows a conventional computerized ultrasound imaging system which can be programmed to communicate with remote devices over a network in conformance with the DICOM standard. The type of imaging system depicted in FIG. 1 creates two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various subsystems. (In FIG. 1, only the image data transfer paths are depicted.) The operator interface comprises a keyboard, a trackball, a multiplicity of pushbuttons, and other input devices such as sliding and rotary knobs.

During imaging, a long sequence of the most recent images are stored and continuously updated automatically in a cine memory 16. Some systems are designed to save the R- acoustic images (this data path is indicated by the dashed line in FIG. 1), while other systems store the X-Y video images. The image loop stored in cine memory 16 can be reviewed via trackball control, and a section of the image loop can be selected for hard disk storage.

Figure 2:
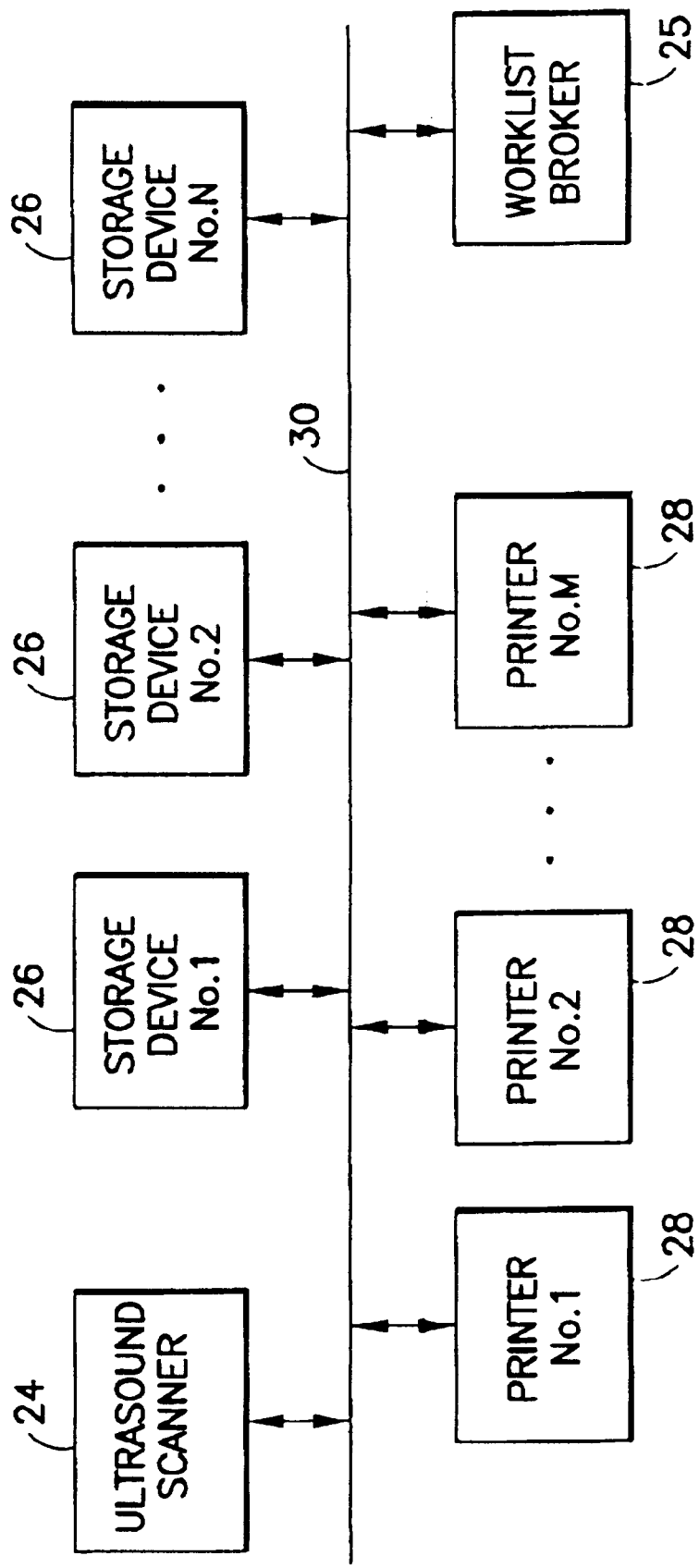
FIG. 2 is a block diagram showing a typical DICOM network.

FIG. 2 generally depicts a simplified DICOM network having an ultrasound scanner 24, a worklist broker (e.g., an RIS) 25, N storage devices 26, and M printing devices 28, all connected to a local area network (LAN) 30. It will be readily appreciated that this diagram represents a simplified example of a DICOM network and that an actual DICOM network in the real world will have many more devices connected to the LAN, including modalities other than ultrasound imaging systems. The present invention is incorporated in an ultrasound imager (scanner) having the built-in capability to communicate with any one or more of the devices 25, 26 and 28 in conformance with the DICOM requirements. As used herein, the term "storage device" includes, but is not limited to, a picture archiving and communications system (PACS) having a viewing station.

Figure 3:
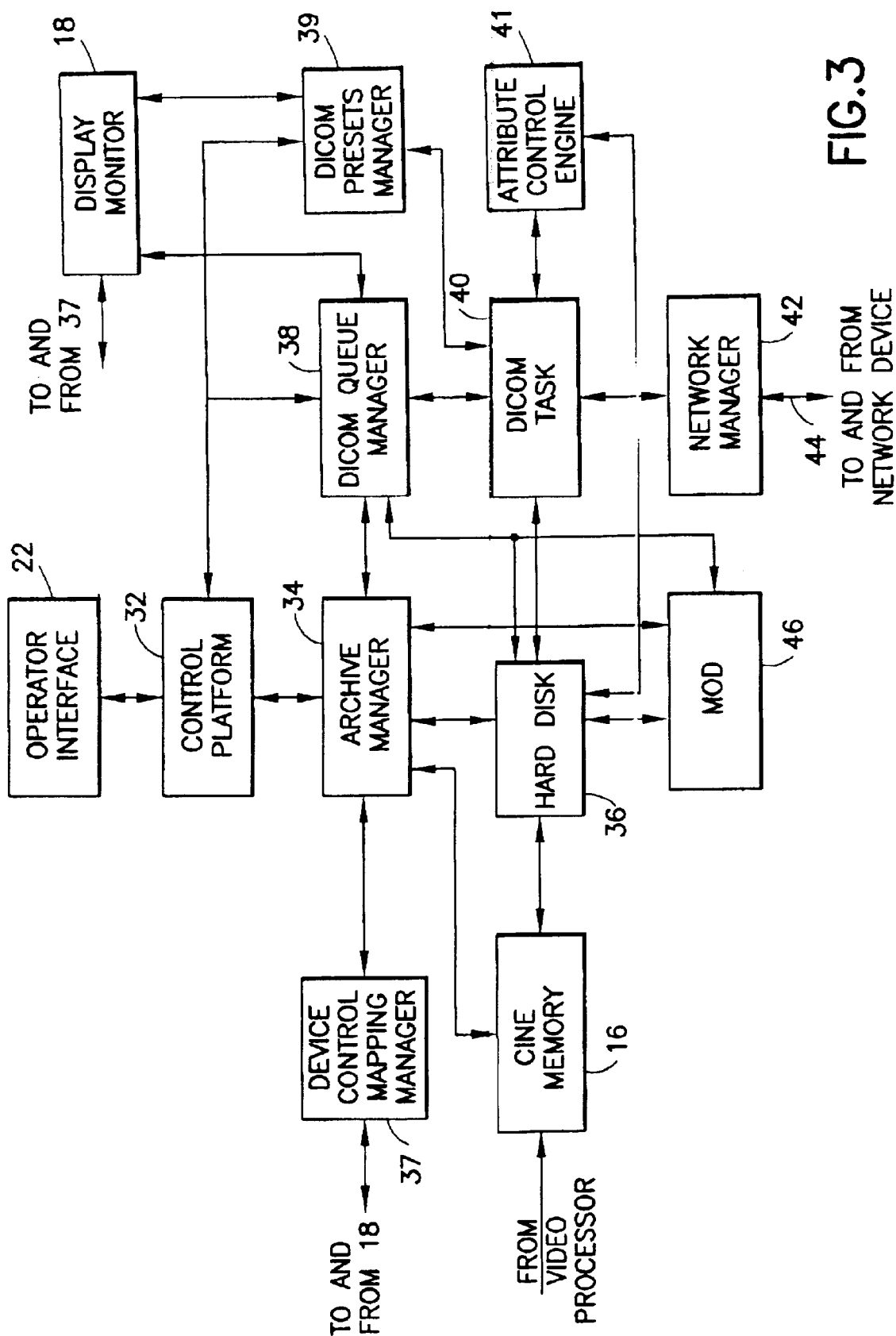
FIG. 3 is a block diagram generally depicting the hardware and software of an ultrasound imaging system in accordance with the preferred embodiment.

A portion of the ultrasound imager is generally depicted in FIG. 3. At the outset it should be appreciated that all of the blocks depicted in FIG. 3, with the exceptions of the cine memory 16, the display monitor 18 and the operator interface 22, are preferably, but not necessarily, incorporated in the host computer (depicted in FIG. 1 as block 20). It should be further appreciated that blocks 32, 34, and 37–42 in FIG. 3 are preferably, but not necessarily, implemented as software.

In the system depicted in FIG. 3, commands inputted via the operator interface 22 are detected and processed by a control platform 32. In return, the control platform will provide signals to the operator interface which activate various visual indicators on the operator interface to indicate the status of various functions. In response to manipulation of the appropriate key or appropriate set of keys by the operator, the DICOM presets manager 39 will display a "Device Configuration" menu (shown in FIG. 4) on the display monitor 18. The operator then enters configuration data for the first destination remote device (e.g., "Printer A" in FIG. 4) via the operator interface. Depending on whether the device being configured is a printer or storage device, the Device Type field 48 on the Device Configuration menu will be filled in with either a "Printer" or a "Storage" entry. If the device being configured is a printer which prints multi-image film sessions, then the Format field 52 in the "Printer Setup" section on the Device Configuration menu will be filled in with numbers indicating the printing format of the multi-image printer (e.g., "3×5" in the case of Printer A). For single-image printers, the entry in Format field 52 will be "1×1". A separate page of the "Device Configuration" menu will be "filled in" for each remote device which the operator wishes to configure.

The imager shown in FIG. 3 is designed to communicate with a configured remote device only if that device has been "activated". Activation causes the DICOM presets manager 39 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

One way of activating a remote device is to click on the Activate field 50 on the Device Configuration menu (see FIG. 4) to toggle the "Activate" state on. A second click on field 50 will toggle the "Activate" state off, and so forth. Alternatively, the operator can call up the Device Activation menu shown in FIG. 5, which is sent to the display monitor by the DICOM presets manager 39. The Device Activation menu comprises a list of the names of all configured remote devices, whether activated or not. A respective Activation field 54 is associated with each named device. Each Activation field 54 is a virtual representation of an Activation toggle switch. In other words, the imager is programmed with software which allows the user to activate and de-activate each configured device by simply clicking on its associated Activation field. A Yes or No is displayed in the Activation field to provide a visual indication of whether the remote device is activated. FIG. 5 assumes that the remote devices named Printer A, Printer B and Storage A have been configured and activated, while the remote devices named Printer X, Printer Y and Storage B have been configured and not activated.

Referring again to FIG. 3, the preferred embodiment is equipped with a plurality of Print/Store buttons on the operator interface 22. Each Print/Store button can be configured by the device control mapping manager 37 to initiate image transfer to more than one remote device, e.g., when a particular Print/Store button is pressed, the computer will send the corresponding acquired image to all activated remote devices configured for that button. The device control mapping manager is programmed to retrieve a Device Control menu, which is a virtual representation of the various configurations for the Print/Store buttons, from the hard disk 36 and send it to the display monitor 18. Each control state can be configured so that the data of the acquired image is expressed as either color intensity values or gray-scale intensity values; so that the acquired image will be stored on the hard disk or the MOD; so that the acquired image will be transferred to one or more activated remote devices; or any combination of these options. Each Print/Store button configuration can be set via the operator interface. For each remote device configured to a particular Print/Store button, pressing that button after freezing an image will cause the associated DICOM task to retrieve an image file having a copy of that image from the hard disk and convert that image file to a DICOM object compatible with the associated remote device.

In accordance with the preferred embodiment, the device control mapping manager 37 (see FIG. 3) constructs a mapping of DICOM tasks (configured for respective remote devices) to Print/Store buttons. In other words, when the operator interacts with the Device Control menu (not shown) to configure a Print/Store button to a particular remote device, the device control mapping manager then identifies the DICOM task corresponding to that remote device and includes it in the device control mapping. The device control mapping manager 37 provides the device control mapping to the archive manager 34. When the archive manager later receives a posting from the control platform 32 that a particular Print/Store button has been pressed, the archive manager 34 will then refer to the device control mapping and determine the DICOM tasks associated with that button from the mapping. The archive manager 34 then advises the DICOM queue manager 38 which DICOM tasks 40 need to construct objects incorporating the selected image frame. The DICOM queue manager 38 then copies that image file once for each task and, if the remote devices are storage devices or single-image printers, adds a job element to the Active Queue of each task. For multi-image printers, the DICOM queue manager 38 need only add another image file name to the Image File Name field of an existing job element in the queue.

Although FIG. 3 depicts only one DICOM task, in accordance with the preferred embodiment, the imager is programmed with multiple DICOM tasks. In the preferred embodiment, one DICOM task is dedicated to worklist management and ten DICOM tasks can be configured to convert image files into either DICOM print objects or DICOM storage objects. It should be appreciated, however, that the present invention is not restricted to having ten DICOM tasks for printing and storage. In response to pressing of a Print/Store button which is configured for multiple remote devices, a corresponding multiplicity of DICOM tasks will be started substantially simultaneously. These concurrently running tasks are performed using conventional multi-tasking principles.

In accordance with the preferred embodiment, the host computer of the imager is programmed to store in memory the configuration data input via the Device Configuration menu shown in FIG. 4. For each configured remote device which is activated, a respective DICOM task is configured by the DICOM presets manager 39 in accordance with the stored configuration data. In other words, each DICOM task is partly defined by the inputs to the corresponding page of the Device Configuration menu. In particular, each DICOM task is programmed to convert an image file into a print object for printers, if "Printer" was entered in the Device Type field 48 (see FIG. 4) on the Device Configuration menu, and into a storage object for storage devices, if "Storage" was entered in the Device Type field. In the case where more than one remote device is designated to receive the same image, the associated DICOM tasks will convert respective copies of that image into respective DICOM objects acceptable to the respective remote devices.

At the beginning of every exam the system user (sonographer or sonologist) pushes a "New Patient" button, causing a "New Patient" menu to appear on the screen of the display monitor. The user then enters information about the patient (e.g., name, patient identifier, accession number, birthdate, etc.). When data entry is completed, the user exits the menu. At this time, a DICOM Study Instance unique identifier (UID) is created. This Study Instance UID forms the base of a Service Object Pair (SOP) Instance UID which tells the receiving DICOM device (SCP) that the image received belongs to a particular patient. Every image taken by the user, after exiting the "New Patient" menu, will have the same UID.

The examination may then begin. The user will scan the patient as needed. The user, at any time, can freeze the image and take a snapshot of that image to send to a remote device. If the receiving device is a printer, the Instance UID is not of any concern. Printers may be configured to put more than one image on a piece of film (e.g., 3×5=15 images). If this were the case, the user would normally take all 15 images before sending the completed film session to the printer.

If the receiving device is a storage device, then the SOP Instance UID will direct the image to that patient's folder of images. Storage devices receive images one at a time. The typical method of image transfer to a storage device is as follows: the DICOM task opens an association (connection) with the receiving storage device; transfer negotiations occur; the image is transferred; and the association is closed. Alternatively, the imager can be configured to open the association once and keep it open throughout the entire exam. In the latter case, the association is opened upon the sending of the first image and is closed by pressing an "End Exam" key.

The image transfer procedure used in the preferred embodiment will be described in more detail with reference to FIG. 3. In response to a request from the operator to archive a frozen image, the control platform 32 sends an "Image Store" instruction to the archive manager 34. In response to the "Image Store" instruction, the archive manager retrieves the frozen image from cine memory 16 and stores it either on the hard disk 36 or on the MOD 46, depending on the system operator's selection.

In addition, the system operator may request that the frozen image be sent to an activated remote device for printing or storage by pressing the appropriate Print/Store button. In response to a request from the operator to transfer a frozen image to a remote device, the control platform 32 sends an "Image Send" instruction to the archive manager 34. The archive manager 34 retrieves the frozen image from the cine memory 16 and stores it in a file on the hard disk 36. The file includes the image pixel data as well as certain attribute data, such as patient name, patient ID, gray-scale or color image, number of rows and columns of pixels, etc. Then the archive manager 34 notifies the DICOM queue manager 38 of the image to be transferred and the destination remote device that image (and subsequent images of the same job) will go to. Next the queue manager 38 copies the image to another location on the hard disk and gives that copied image a new file name. If the pressed Print/Store button is configured for multiple remote devices, then the queue manager 38 will store multiple copies of the frozen image in multiple files, i.e., a separate copy of the frozen image for each remote device designated as a destination for that image.

In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object.

In accordance with the preferred embodiment of the present invention, each DICOM task 40 has a respective pair of Attribute Control Files associated therewith, one which, at the time of installation) is compliant with the DICOM 98 standard and another which is compliant with the DICOM 99 standard. In accordance with the preferred embodiment of the present invention, for each DICOM task the system user is able to select one of the two available Attribute Control Files to configure that DICOM task. This is accomplished using the "Active Device Configuration" menu shown in FIG. 6.

In accordance with the preferred embodiment, each DICOM task can be configured by clicking on the IHE Tags field 56 on the Active Device Configuration menu (see FIG. 6) to toggle the IHE Attribute Control File on and the DICOM 98 Attribute Control File off. A second click on field 56 will toggle the IHE Attribute Control File off and the DICOM 98 Attribute Control File on, and so forth. The Active Device Configuration menu shown in FIG. 6 is sent to the display monitor by the DICOM presets manager 39. The Active Device Configuration menu comprises a list of the names of all activated remote devices. A respective Attribute Control File activation field 56 is associated with each named remote device. Each field 56 is a virtual representation of a toggle switch. In other words, the imager is programmed with software which allows the user to configure each DICOM task by simply switching back and forth between alternative Attribute Control Files, one of which (i.e., the IHE Attribute Control File containing the IHE-compliant tags) will be visually indicated by the entry ON in field 56 in FIG. 6, while the other (the Attribute Control File which is not compliant with the IHE standard) will be visually indicated by the entry OFF (i.e., the IHE Attribute Control File is off) in field 56.

It should be appreciated that the IHE-compliant tags are not specific to IHE, but are simply tags that are used by IHE and have been found to cause trouble with many existing devices. The actual commercial product will refer to them as the "IHE Tags" in the menu shown on FIG. 6 so that the institution can identify whether or not their devices will accept these new tags by simply knowing that their devices subscribe to the IHE technical framework.

In accordance with the preferred embodiment of the present invention, each DICOM task 40 constructs DICOM objects by associating attribute names and values with attribute tags identified in a selected one of a pair of Attribute Control Files as being compatible with the destination remote device. The user can select either one of the two Attribute Control Files, depending on the requirements of the particular remote device to which the image is being transferred, by the simple expedient of operating a switch on the user interface screen shown in FIG. 6.

In accordance with the preferred embodiment, each DICOM task 40 has two Attribute Control Files associated therewith stored on the hard disk 36. Each Attribute Control File identifies the attribute tags required for compatibility with respective communications standards. As in the case of the DICOM 98 and DICOM 99 standards, one communications standard has different attribute tags than the other. The concept of the invention can be extended to include any number of Attribute Control Files per DICOM task.

In accordance with a further feature of the preferred embodiment, the host computer is programmed with an Attribute Control Engine 41 which controls which attributes to include and which attribute names and values to associate with which attribute tags in the DICOM objects constructed by each DICOM task 40. When the system is powered up, the Attribute Control Engine 41 reads the Attribute Control Files from the hard disk 36 and writes them into system memory. These Attribute Control Files are kept in system memory for the duration of the power cycle. Each Attribute Control File comprises many lines for setting up the DICOM attributes. One line is needed to set up one DICOM attribute. The format of each line is as follows:

[Module Name] [Tag Number] [Sequence Number] [Format String]

The module name specifies the DICOM module which the attribute on that line belongs to. The module name is a defined term. The tag number specifies a particular attribute included in that module. Some DICOM attributes have the sequence of the subset of some DICOM attributes. The sequence number specifies the sequence which the attribute belongs to. The format string specifies how the data value of the attribute should be created.

Each DICOM task 40 receives a control signal from the DICOM presets manager 39 indicating which of the two Attribute Control Files associated with that DICOM task has been selected by the system user. Each DICOM task 40 must then receive instructions from the Attribute Control Engine 41 concerning which attributes to include and which attribute tags to use in the DICOM object being constructed by that DICOM task, the tags being the tag numbers stored in the selected Attribute Control File. First, the DICOM task 40 asks the Attribute Control Engine 41 whether a particular attribute should be included in the DICOM object. The Attribute Control Engine 41 refers to the selected Attribute Control File to determine whether the attribute should be included. If the attribute should not be included, the Attribute Control Engine 41 advises the DICOM task accordingly. The DICOM task 40 then proceeds to the next attribute. If the attribute should be included in the DICOM object under construction, the Attribute Control Engine 41 so advises the DICOM task 40. The DICOM task then asks the Attribute Control Engine 41 whether the value of that attribute should be obtained from the image file which is being converted or whether the attribute value should be obtained from the selected Attribute Control File. Again the Attribute Control Engine 41 refers to the selected Attribute Control File. If the attribute value should be taken from the image file, the Attribute Control Engine so advises the DICOM task. Alternatively, if the attribute value should be taken from the selected Attribute Control File, the Attribute Control Engine 41 retrieves that attribute value and sends it to the DICOM task 40.

The foregoing procedure is repeated for each attribute associated with the particular function, i.e., construction of a print object or storage object, being performed by a particular DICOM task. In other words, if the DICOM task is performing the storage function, then the DICOM task will query the Attribute Control Engine with regard to only those attributes which are relevant to the storage function.

Likewise for the print function. In response to each query from the DICOM task 40 regarding a particular attribute, the Attribute Control Engine 41 will read only that line in the selected Attribute Control File corresponding to that attribute.

Referring again to FIG. 3, each DICOM task 40 sends its DICOM object in proper format to the corresponding destination remote device via the network manager 42 and the port 44. The DICOM tasks run concurrently and independently of each other in accordance with conventional multi-tasking principles. Jobs which are waiting to be converted into DICOM objects by a DICOM task are queued. The queue is managed by a DICOM queue manager 38.

Referring again to FIG. 3, the first job in the queue is sent by the queue manager 38 to the DICOM task 40 identified by the Task ID and corresponding to the destination remote device for that first job. When the DICOM task 40 receives a job from the queue, it will read a pointer which contains the file name of the image to be formatted and transferred to the destination remote device. The DICOM task 40 then retrieves the image from the named file on the hard disk and reformats it into the appropriate DICOM object in accordance with the instructions from the Attribute Control Engine 41. In addition to the pixel data for the image being transferred, the DICOM object constructed by the DICOM task will include attribute data in DICOM format. If the remote device is a storage device, the DICOM task will also attach a UID to the image.

Next the DICOM task 40 will open a connection (association) to the destination remote device and negotiate a syntax. In particular, the DICOM task 40 sends a request via the network manager 42 and a port 44 that an association with the configured remote device be opened. If the remote device responds affirmatively and if a communications syntax is agreed upon, the association is opened. Once the association is open and assuming that a channel on the network is available (i.e., the network is not busy), the image is sent from the imager onto the network, again via network manager 42 and port 44. If the destination remote device sends back a message that the image transfer was successful, then the DICOM task 40 notifies the queue manager 38. The queue manager then removes the entry for the successfully transferred image from the queue and deletes that image file from the hard disk 36.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. An imaging system comprising:
   a networking port for communicating with a first remote device on a network;
   an image acquisition subsystem for acquiring frames of image data;
   memory storing acquired frames of image data in respective image files and storing first and second sets of attribute data in first and second attribute control files respectively, said first and second sets of attribute data being compliant with first and second communications standards respectively;
   a first user-operable switch for selecting the one of said first and second attribute control files which corresponds to the one of said first and second communications standards with which said first remote device is compliant;
   a first object constructing task for constructing data objects with data from said image files and attribute data from said selected one of said first and second attribute control files, said first and second attribute control files being associated with said first object construction task;
   an attribute control engine which communicates said attribute data from said selected one of said first and second attribute control files to said first object constructing task; and
   a network manager for transferring data objects from said first object constructing task to said networking port destined for said remote device.

2. The imaging system as recited in claim 1, wherein said memory stores third and fourth sets of attribute data in third and fourth attribute control files respectively, said third and fourth sets of attribute data corresponding to said first and second communications standards respectively, further comprising:
   a second user-operable switch for selecting the one of said third and fourth attribute control files which corresponds to the one of said first and second communications standards with which a second remote device on said network is compliant; and
   a second object constructing task for constructing data objects with data from said image files and attribute data from said selected one of said third and fourth attribute control files, said third and fourth attribute control files being associated with said second object constructing task,
   wherein said attribute control engine communicates said attribute data from said selected one of said third and fourth attribute control files to said second object constructing task, and said network manager transfers data objects from said second object constructing task to said networking port destined for said second remote device.

3. The system as recited in claim 2, wherein said first and second user-operable switches comprise virtual toggle switches displayed on a user interface screen, each of said virtual toggle switches having first and second states.

4. The system as recited in claim 2, wherein said second and fourth attribute control files are identical.

5. The system as recited in claim 1, wherein said first attribute control file comprises a first set of DICOM tag numbers and said second attribute control file comprises a second set of DICOM tag numbers, said first and second sets of DICOM tag numbers being not identical.

6. The system as recited in claim 5, wherein one of said first and second sets of DICOM tag numbers is compliant with said first remote device and the other of said first and second sets of DICOM tag numbers is not compliant with said first remote device.

7. A system comprising:
   a networking port for communicating with a remote device on a network;
   memory storing frames of image data in respective image files and storing first and second sets of attribute data in first and second attribute control files respectively, said first and second sets of attribute data being compliant with first and second communications standards respectively;

an operator interface comprising a graphical user-interface menu for selecting one of said first and second attribute control files which corresponds to the one of said first and second communications standards with which said remote device is compliant;

an object constructing task for constructing data objects with data from said image files and attribute data from said selected one of said first and second attribute control files, said first and second attribute control files being associated with said object constructing task; and a network manager for transferring data objects from said object constructing task to said networking port destined for said remote device.

8. The system as recited in claim 7, wherein said graphical user-interface menu comprises a virtual toggle switch having first and second states.

9. The system as recited in claim 8, wherein said first attribute control file comprises a first set of DICOM tag numbers and said second attribute control file comprises a second set of DICOM tag numbers, said first and second sets of DICOM tag numbers being not identical.

10. The system as recited in claim 9, wherein one of said first and second sets of DICOM tag numbers is compliant with said remote device and the other of said first and second sets of DICOM tag numbers is not compliant with said remote device.

11. The system as recited in claim 7, further comprising an attribute control engine which communicates said attribute data from said selected one of said first and second attribute control files to said object constructing task.

12. An imaging system comprising:

a networking port for communicating with a plurality of remote devices on a network;

an operator interface comprising a graphical user-interface menu for selecting one of first and second communications standards which a selected one of said plurality of remote devices is compliant with;

an image acquisition subsystem for acquiring frames of image data;

an object constructing task for constructing data objects from frames of image data and from attribute data which is compliant with said selected one of said first and second communications standards; and a network manager for transferring said data objects from said object constructing task to said networking port destined for said selected one of said plurality of remote devices.

13. The system as recited in claim 12, wherein said graphical user-interface menu comprises a plurality of virtual toggle switches corresponding to said plurality of remote devices, each of said virtual toggle switches having first and second states.

14. The system as recited in claim 12, wherein said graphical user-interface menu comprises a plurality of identifiers, each identifier identifying a respective one of said plurality of remote devices, and a plurality of spaces activatable by clicking, each space being activatable for selecting a communications standard to enable said imaging system to communicate with a respective identified remote device.

15. The system as recited in claim 12, wherein said first communications standard requires inclusion of a first set of tag numbers in each constructed data object and said second communications standard requires inclusion of a second set of tag numbers in each constructed data object, said first and second sets of tag numbers being not identical.

16. The system as recited in claim 15, further comprising an attribute control engine which communicates said first set of tag numbers to said object constructing task if said first communications standard has been selected via said graphical user-interface menu, and which communicates said second set of tag numbers to said objecting constructing task if said second communications standard has been selected via said graphical user-interface menu.

* * * * *